United States Patent

Hartenstein et al.

[11] 4,202,980
[45] May 13, 1980

[54] PROCESS FOR THE PREPARATION OF 1-HYDROXYAPORPHINE-DERIVATIVES

[75] Inventors: Johannes Hartenstein, Stegen-Wittental; Gerhard Satzinger, Denzlingen, both of Fed. Rep. of Germany

[73] Assignee: Warner-Lambert Company, Morris Plains, N.J.

[21] Appl. No.: 971,142

[22] Filed: Dec. 19, 1978

[30] Foreign Application Priority Data

Dec. 22, 1977 [DE] Fed. Rep. of Germany ....... 2757281

[51] Int. Cl.² ............................................. C07D 221/18
[52] U.S. Cl. ..................................................... 546/75
[58] Field of Search ............................................ 546/75

[56] References Cited

U.S. PATENT DOCUMENTS 3,950,344  4/1976  Kupchan ................................. 546/75

Primary Examiner—Paul M. Coughlan, Jr.
Attorney, Agent, or Firm—George M. Kaplan; Albert H. Graddis

[57] ABSTRACT

A process for the preparation of 1-hydroxyaporphine derivatives of the general formula:

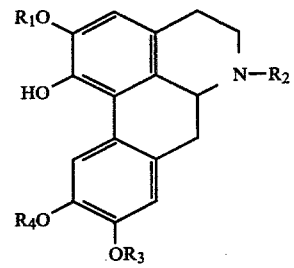

I wherein $R_1$, $R_3$ and $R_4$, which are the same or different, are lower alkyl, aryl or aralkyl radicals or $R_3$ and $R_4$ can together form a lower alkylene bridge member and $R_2$ is a hydrogen atom or a lower alkyl, aralkyl or alkoxycarbonyl radical or an acyl radical derived from an aliphatic, aromatic or araliphatic carboxylic acid.

9 Claims, No Drawings

PROCESS FOR THE PREPARATION OF 1-HYDROXYAPORPHINE-DERIVATIVES

The present invention is concerned with a process for the preparation of 1-hydroxyaporphine derivatives.

Oxidative phenol couplings of 7-hydroxy-1,2,3,4-tetrahydroisoquinolines for the preparation of aporphines have already been described. Thus, for example, the oxidation of (±)-codamine of the following formula:

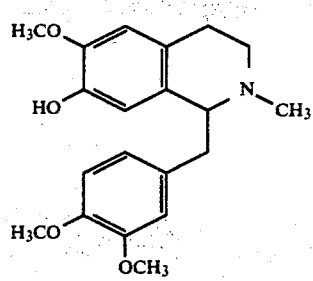

by means of lead tetraacetate gives (±)-4α- and -4β-acetoxy-O-acetylthaliporphine (see Chem. Pharm. Bull., 23, 2578/1975). Oxidation of (±)-codamine with vanadyl trifluoride in methylene dichloride/TFA (see S. M. Kupchan et al., J. Org. Chem., 41, 4049/1976) gave "a complex mixture of products" from which could only be isolated (±)-thalicmidine of the formula:

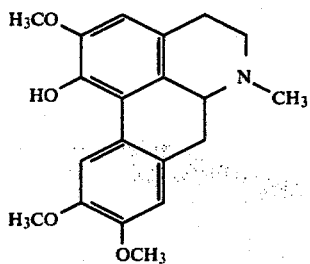

(I)

in a yield of 38%. Using a borane complex of codamine admittedly increases the yield of (±)-thalicmidine to 80% but two additional process steps are then necessary.

German Patent specification No. 2,625,116 also describes an oxidative cyclisation reaction of structurally analogous tetrahydroisoquinolines, using vanadyl trifluoride as oxidation agent. However, this reaction leads to aporphine derivatives which are all hydroxylated in the 4-position. Thus, by means of vanadyl trifluoride, there is not only brought about an oxidative ring closure reaction but, at the same time, a hydroxylation in the non-aromatic part of the ring system. This reaction was also to have been expected in the present case.

Surprisingly, however, we have now found that 7-hydroxy-1,2,3,4-tetrahydroisoquinoline derivatives can be oxidised by vanadyl trichloride smoothly and completely, without the introduction of a protective group on the nitrogen atom, to give 1-hydroxyaporphines which are not hydroxylated in the aliphatic part of the ring system. It is hereby of advantage that vanadyl chloride is inexpensive and, because of its very good solubility in organic solvents, is particularly easy to handle on a large scale.

Thus, according to the present invention, there is provided a process for the preparation of 1-hydroxyaporphine derivatives of the general formula:

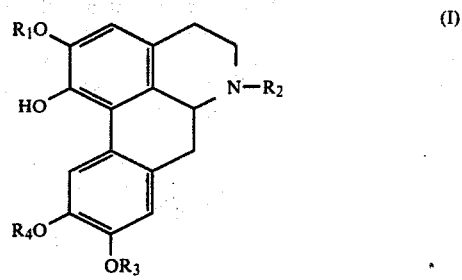

(I)

wherein $R_1$, $R_3$ and $R_4$, which are the same or different, are lower alkyl, aryl or aralkyl radicals or $R_3$ and $R_4$ can together form a lower alkylene bridge member and $R_2$ is a hydrogen atom or a lower alkyl, aralkyl or alkoxycarbonyl radical or an acyl radical derived from an aliphatic, aromatic or araliphatic carboxylic acid, wherein a compound of the general formula:

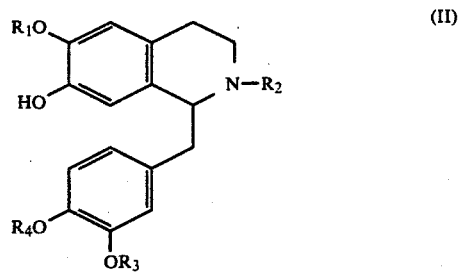

(II)

in which $R_1$, $R_2$, $R_3$ and $R_4$ have the same meanings as above, is oxidised in the presence of a strong acid with an at least equivalent amount of vanadyl chloride.

According to the present invention, the lower alkyl radicals contain up to 5 and preferably up to 3 carbon atoms, the lower aralkyl radicals are phenalkyl radicals containing 7 to 10 carbon atoms, the aliphatic carboxylic acids are to be understood to be mono- and dibasic acids containing up to 5 carbon atoms and the araliphatic acids to be phenylalkane carboxylic acids containing 8 to 11 carbon atoms.

The process according to the present invention is especially suitable for compounds in which $Rd_1$, $R_3$ and/or $R_4$ are methyl, ethyl, phenyl or benzyl radicals and in which $R_3$ and $R_4$ together can also represent a methylene or ethylene radical; $R_2$ is preferably a hydrogen atom or a methyl, ethyl, propyl, phenyl, benzyl, formyl, acetyl, trifluoroacetyl, benzoyl, methoxycarbonyl or ethoxycarbonyl radical.

The most important and interesting compounds which can be obtained by the process according to the present invention contain the following radicals: $R_1$, $R_3$ and $R_4$ are methyl radicals or $R_3$ and $R_4$ together represent a methylene radical; and $R_2$ is a hydrogen atom or a methyl or trifluoroacetyl radical.

In the case of oxidising (±)-N-trifluoroacetylnorcodamine (II: $R_1=R_3=R_4=$methyl; $R_2=-$COCF$_3$) with vanadyl chloride, it is found from the thin layer chromatographic analysis of the reaction mixture that at −15° C., even after only 5 minutes, the reaction is practically quantitative, without by-products being formed.

For carrying out the process according to the present invention, the 7-hydroxy-1,2,3,4-tetrahydroisoquinoline derivatives of general formula (II) are dissolved in an organic solvent which is inert under the reaction conditions and reacted in the presence of at least one equivalent and preferably in an excess of a strong acid at a temperature of from −70° C. to ambient temperature and preferably at −20° to −5° C. with at least an equivalent and preferably with an excess amount of vanadyl chloride.

The inert solvent used is preferably a chlorinated hydrocarbon, especially methylene chloride, chloroform, dichloroethane or carbon tetrachloride.

Examples of acids which can be used include inorganic acids, such as hydrochloric acid, hydrobromic acid and perchloric acid, and strong organic acids, which can possibly also serve at the same time as solvents.

The vanadyl chloride can be used in a mole ratio of 1–3 and preferably of 1.3 to 2.5 per mole of tetrahydroisoquinoline.

If desired, the vanadyl chloride can be used in a chemically inert solvent which dissolves the tetrahydroisoquinoline.

When the vanadyl chloride is added to the reaction mixture, a momentary coloration of the reaction mixture to dark green-dark blue occurs.

Thin layer chromatographic monitoring of the reaction shows that the oxidative cyclisation has taken place practically quantitatively after 5 to 15 minutes.

In order to isolate the reaction products, the reaction mixture can be evaporated in a vacuum and the residue partitioned between water and an organic solvent, possibly with rendering alkaline with ammonia or with sodium carbonate or bicarbonate. Working up the extract in the usual manner then gives the crude product which can be purified by crystallisation and/or chromatography. The working up can be carried out especially advantageously when using trifluoroacetic acid. In the case of this variant of the process, the reaction products of general formula (I), insofar as they contain a basic nitrogen atom ($R_2$ not acyl), can, as a rule, be isolated in pure form as readily crystallising salts of trifluoroacetic acid and purified as such. For this purpose, the reaction mixture, after stripping off the trifluoroacetic acid and possibly the solvent, is taken up in water and extracted with chloroform in which the trifluoroacetates are, surprisingly, readily soluble. This procedure permits an especially easy separation of the products from the vanadium salts, whereas, under basic conditions, the formation of precipitates from vanadium salts makes the partitioning and isolation considerably more difficult.

The compounds obtained by the process according to the present invention are valuable intermediates, for example for the preparation of pharmaceuticals.

The 7-hydroxy-1,2,3,4-tetrahydroisoquinolines used as starting materials can be prepared by the methods described in the literature (cf. J. Org. Chem., 41, 4050, footnote 6/1976) and can be used either as enantiomers or as mixtures of enantiomers.

The following Examples are given for the purpose of illustrating the present invention:

EXAMPLE 1

(±)-1-Hydroxy-2,9,10-trimethoxyaporphine ((±)-thalicmidine)

0.9 g. (2.63 mol) (±)-7-hydroxy-6-methoxy-2-methyl-1-veratryl-1,2,3,4-tetrahydroisoquinoline ((±)-codamine) (preparation see Tetrahedron, 23, 2563/1967) are dissolved in 10 ml. trifluoroacetic acid and cooled to −10° C., with the exclusion of moisture. At this temperature and in an atmosphere of nitrogen, there is added dropwise, while stirring, a solution of 0.6 ml. (1.1 g; 6.4 mMol) vanadyl trichloride in 5 ml. anhydrous methylene chloride within the course of about 1 minute. The reaction mixture momentarily becomes dark blue. When the dropwise addition is completed, stirring is continued at −10° C. for a further 10 minutes, whereafter the trifluoroacetic acid and the solvent are distilled off at ambient temperature in a vacuum. The residue is mixed with ice water and extracted with chloroform. After drying the extract over anhydrous sodium sulphate, stripping off the solvent in a vacuum and crystallising the residue from acetoneether, there are obtained 840 mg. (70% of theory) (±)-1-hydroxy-2,9,10-trimethoxyaporphine in the form of its crystalline, red-brown trifluoroacetate; m.p. 193°–200° C.

A further 100 mg. fraction of the trifluoroacetate can be obtained from the mother liquor. The total yield of crystalline product is 78.5% of theory.

By treatment with ammonia and crystallisation from ethanol/diethyl ether, there is obtained (±)-thalicmidine in the form of blackish crystals; m.p. 183°–186° C.; MS: M+ 341.

Comparative experiment (reaction with vanadyl trifluoride)

0.9 g. (2.63 mMol) (±)-7-Hydroxy-6-methoxy-2-methyl-1-veratryl-1,2,3,4-tetrahydroisoquinoline in 10 ml. trifluoroacetic acid are mixed dropwise at −10° C., with stirring and under a protective gas atmosphere, within the course of 5 minutes with a solution of 800 mg. (6.4 mMol) vanadyl trifluoride in 50 ml. trifluoroacetic acid. Stirring is continued for 5 minutes at −10° C., whereafter the reaction mixture is worked up in the manner described above. Crystallisation from acetone/diethyl ether gives a product melting at 185°–195° C.

Thin layer chromatographic analysis (chloroformmethanol 95:5 v/v; silica gel; detection with cerium sulphate/sulphuric acid) shows that, besides (±)-thalicmidine, there has also been formed a further compound with a similar $R_f$ value. The NMR spectrum (DMSO-$d_6$) and the mass spectrum also confirm the presence of a mixture consisting substantially of two components. The molecular ion of the second compound is m/e 357 and thus has a molecular weight which is 16 mass units higher. On the basis of the chemical and spectroscopic properties, it is (±)-4-hydroxythalicmidine.

EXAMPLE 2

(±)-1-Hydroxy-2,9,10-trimethoxy-N-noraporphine ((±)-N-northalicmidine)

1 g. (3 mMol) (±)-N-norcodamine (preparation cf. J. Org. Chem., 41, 4049/1976) is dissolved in 10 ml. trifluoroacetic acid and mixed dropwise at −10° C., under a protective gas atmosphere, with a solution of 0.35 ml. (0.57 g.; 3.3 mMol) vanadyl trichloride in 5 ml. anhydrous methylene chloride. Thereafter, the reaction mixture is stirred for a further 15 minutes at −10° C. and evaporated in a vacuum at ambient temperature and the residue is taken up in water and extracted with chloroform. Working up the extract in the usual manner and crystallising from acetone gives 730 mg. (55% of theory) (±)-1-hydroxy-2,9,10-trimethoxy-N-noraporphine in the form of its trifluoroacetate; m.p. 198°–209° C.

MS: 327 (M-CF$_3$COOH);

IR: 1670 cm$^{-1}$; NMR (DMSO-a$_6$): 3.76, 3.83, 3.87 (each 1 OCH$_3$,s), 6.82, 7.00, 8.11 (each 1H, s).

EXAMPLE 3

(±)-N-Trifluoroacetyl-1-hydroxy-2,9,10-trimethoxy-N-noraporphine 3 g. (7.1 mMol) (±)-N-trifluoroacetyl-7-hydroxy-6-methoxy-1-veratryl-1,2,3,4-tetrahydroisoquinoline (cf. J. Org. Chem., 41, 4049/1976) in 30 ml. trifluoroacetic acid are mixed dropwise at −10° C., under an atmosphere of nitrogen, with a solution of 1.65 ml. (3.03 g.; 17.48 mMol) vanadyl chloride in 15 ml. anhydrous methylene chloride within the course of 2 minutes. The thin layer chromatographic analysis shows that even after 5 minutes practically no more starting material is present. Working up in the manner described in Example 1 and crystallisation from acetone-diethyl ether gives, in two portions, 2.64 g. (88% of theory) crystalline (±)-N-trifluoroacetyl-1-hydroxy-2,9,10-trimethoxy-N-noraporphine in the form of dark brown crystals; m.p. 210°–222° C.

EXAMPLE 4

(±)-N-Trifluoroacetyl-1-hydroxy-2-methoxy-9,10-methylenedioxy-N-noraporphine 2 g. (4.9 mMol) (±)-N-Trifluoroacetyl-7-hydroxy-6-methoxy-1-(3,4-methylenedioxybenzyl)-1,2,3,4-tetrahydroisoquinoline in a mixture of 10 ml. trifluoroacetic acid and 10 ml. anhydrous methylene chloride are mixed dropwise at −10° C. with a solution of 0.94 ml. (1.73 g., 10 mMol) vanadyl chloride in 10 ml. anhydrous methylene chloride. According to the thin layer chromatographic analysis, after only 5 minutes no more starting material is present. The reaction is evaporated in a vacuum and recrystallised from methanol-acetone-water to give (±)-N-trifluoroacetyl-1-hydroxy-2-methoxy-9,10-methylenedioxy-N-noraporphine.

Yield 1.72 g. (86.6% of theory); m.p. 282°–284° C.

MS: M+ 407.

What we claim is:

1. Process for the preparation of 1-hydroxy-aporphine derivatives of the general formula:

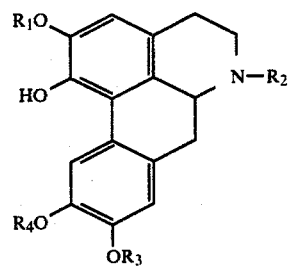

in which R$_1$, R$_3$ and R$_4$, which can be the same or different, are lower alkyl, aryl or aralkyl radicals or R$_3$ and R$_4$ can together form a lower alkylene bridge member and R$_2$ is a hydrogen atom or a lower alkyl, aralkyl or alkoxycarbonyl radical or an acyl radical derived from an aliphatic, aromatic or araliphatic carboxylic acid, wherein a tetrahydroisoquinoline compound of the general formula:

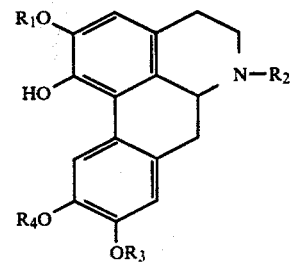

in which R$_1$, R$_2$, R$_3$ and R$_4$ have the same meanings as above, is oxidised in the presence of a strong acid with at least an equivalent amount of vanadyl chloride.

2. Process according to claim 1, wherein the reaction is carried out in the presence of a chemically inert solvent.

3. Process according to claim 2, wherein the inert solvent is methylene chloride, chloroform, dichloroethane or carbon tetrachloride.

4. Process according to claim 2, wherein the reaction is carried out with a molar excess of a strong acid.

5. Process according to claim 4, wherein the reaction is carried out at a temperature of from −70° C. to ambient temperature.

6. Process according to claim 5, wherein the reaction is carried out at a temperature of from −20° to −5° C.

7. Process according to claim 2, wherein the vanadyl chloride is used in an amount of from 1 to 3 mole per mole of tetrahydroisoquinoline.

8. Process according to claim 7, wherein the vanadyl chloride is used in an amount of from 1.3 to 2.5 mole per mole of tetrahydroisoquinoline.

9. Process according to claim 4, wherein the strong acid used is trifluoroacetic acid.

\* \* \* \* \*